(12) United States Patent
Ogrin et al.

(10) Patent No.: US 8,405,477 B2
(45) Date of Patent: Mar. 26, 2013

(54) CONTROLLABLE MAGNETIC SYSTEMS

(75) Inventors: Feodor Yurievitch Ogrin, Devon (GB); Peter Georgiev Petrov, Devon (GB); Charles Peter Winlove, Devon (GB)

(73) Assignee: University of Exeter, Exeter, Devon (GB)

( * ) Notice: Subject to any disclaimer, the term of this patent is extended or adjusted under 35 U.S.C. 154(b) by 156 days.

(21) Appl. No.: 12/918,808

(22) PCT Filed: Feb. 22, 2008

(86) PCT No.: PCT/GB2008/050120
§ 371 (c)(1),
(2), (4) Date: Nov. 12, 2010

(87) PCT Pub. No.: WO2009/103938
PCT Pub. Date: Aug. 27, 2009

(65) Prior Publication Data
US 2011/0052393 A1  Mar. 3, 2011

(51) Int. Cl.
*H01F 7/00* (2006.01)
*H01F 1/00* (2006.01)

(52) U.S. Cl. ......... 335/219; 335/296; 335/302; 335/306

(58) Field of Classification Search .......... 335/219, 335/296, 302, 306
See application file for complete search history.

(56) References Cited

U.S. PATENT DOCUMENTS

| | | | |
|---|---|---|---|
| 1,595,801 A * | 8/1926 | McDonald | 446/134 |
| 3,359,152 A * | 12/1967 | Blume, Jr. | 335/302 |
| 3,504,316 A * | 3/1970 | Bekedam | 335/306 |
| 3,876,932 A | 4/1975 | Domon et al. | |
| 3,982,334 A * | 9/1976 | Tate | 434/409 |
| 7,504,921 B2 * | 3/2009 | Vranish | 335/302 |
| 7,578,788 B2 * | 8/2009 | Yokoi et al. | 600/160 |
| 2003/0181788 A1 * | 9/2003 | Yokoi et al. | 600/160 |
| 2007/0210886 A1 * | 9/2007 | Gerber | 335/306 |

OTHER PUBLICATIONS

Arai, K. et al., "Fabrication of Small Flying Machines Using Magnetic Thin Films," *IEEE Transactions on Magnetics*, Nov. 1995, pp. 3758-3760, vol. 31, No. 6.
Ishiyama, K. et al., "Swimming Micro-machine Driven by Magnetic Torque," *Sensors and Actuators A*, Jun. 5, 2001, pp. 141-144, vol. 91, No. 1-2.
PCT International Search Report and Written Opinion, PCT Application No. PCT/GB2008/050120, Dec. 16, 2008, ten pages.
Tomie, M. et al., "Turning Performance of Fish-Type Microrobot Driven by External Magnetic Field," *IEEE Transactions on Magnetics*, Oct. 2005, pp. 4015-4017, vol. 41, No. 10.

* cited by examiner

*Primary Examiner* — Mohamad Musleh
(74) *Attorney, Agent, or Firm* — Fenwick & West LLP (57) ABSTRACT

This invention relates to methods and devices for propulsion through a fluid, in particular at low Reynolds number. We describe a method of propelling one of a magnetic device and a fluid relative to the other, the magnetic device comprising a pair of magnetic moments linked by an elastic coupling element, one of said moments having a greater resistance to a change in orientation due to an external applied magnetic field than the other, the method comprising applying an elliptical or ellipsoidal rotating magnetic field to the device to cause a change in mutual attraction or repulsion between said magnetic moments to thereby change a physical configuration of said device, propelling said device relative to said fluid.

10 Claims, 7 Drawing Sheets

CONTROLLABLE MAGNETIC SYSTEMS

FIELD OF THE INVENTION

This invention relates to controllable magnetic systems, in particular to methods and devices for propulsion through a fluid, especially at low Reynolds number.

BACKGROUND TO THE INVENTION

There is a widespread need in basic biomedical research as well as in applications such as drug delivery and biotechnology for micro-motors that can generate translational motions or induce local strains on cellular or molecular length scales. For example, many areas of biological research involve the application of forces to individual cells or even macromolecules; nanoscale chemistry requires the rapid and directed transport of reagents between compartments in microreactors; and targeted drug delivery is a major aim in the pharmaceutical industry.

The past few decades have seen increased interest in low Reynolds number swimming mechanisms with research along two complementary lines. Firstly, the need to understand how micrometer-sized organisms are able to propel themselves in a world with no inertia has led to important insights, for example the discovery and analysis of the rotating bacterial flagella. The second line is more utilitarian, and aimed at the construction of autonomous microrobots, capable of performing useful functions such as active targeted drug delivery, destroying kidney stones [J. Edd et al. in Proc. IEEE/RSJ Int. Conf. Intelligent Robots and Systems (2003), vol. 3, pp. 2583-2588] or stirring and pumping in microfluidic devices [S. T. Chang et al., Nature Materials 6, 235 (2007)].

A very nice introduction to the physics of motion at low Reynolds number can be found in E. M. Purcell, Am. J. Phys 45, 3 (1977). Broadly speaking the Reynolds number defines the ratio of inertial forces to viscous forces for an object moving through a fluid. The techniques we describe for swimming in a fluid at low Reynolds number preferably relate to a Reynolds number of less than 1, more typically of order $10^{-3}$, $10^{-4}$, or $10^{-5}$. This compares with the Reynolds number for, say, a man swimming in water which is of order $10^4$. In a low Reynolds number environment intuitions about the nature and mechanism of motion are generally wrong, in part because inertia is essentially irrelevant. For example a reciprocal motion, that is one in which a body deforms and then returns to the original shape by going through the deformation in reverse does not result in translation through the fluid. This has been termed the "scallop theorem"—a scallop cannot swim at low Reynolds number because it only has one hinge and is thus bound to make a reciprocal motion. For non-reciprocal motions, which break the time-reversal symmetry, translational motion (swimming) can occur although the direction is often counter-intuitive.

A low Reynolds number swimmer, natural or artificial has two requirements in order to propel itself through the fluid environment. The first is related to the peculiar restrictions arising from the fact that for micrometer-sized swimmer in aqueous environments the fluid flow is dominated by viscous effects. This situation is best illustrated by the aforementioned "scallop theorem"; the trajectory of the swimmer is determined by the sequence of geometrical configurations it assumes (time makes no difference: the pattern of motion is the same whether the change is fast or slow). Self-propulsion is only possible if forward- and backward-motion phases in a full swimming cycle are non-reciprocal, that is not symmetric with respect to time reversal (the motion looks different depending whether it is "played" forwards or backwards). The system should have at least two degrees of freedom in its configurational space or it will perform a reciprocal motion with no net translation. As a result effort has been invested in devising various shape sequences that would lead to translational motion [S. Camalet et al., Phys. Rev. Lett. 82, 1590 (1999); L. E. Becker et al., J. Fluid Mech. 490, 15 (2003); A. Najafi and R. Golestanian, Phy. Rev. E. 69, 062901 (2004); and J. E. Avron et al. New J. Phys. 7, 234 (2004)] and analysing the efficiency of swimming [A Shapere and F. Wilczek, J. Fluid Mech. 198, 557 (1989), ibid 198, 587 (1989); E. M. Purcell, Proc. Natl. Acad. Sci. USA 94, 11307 (1997); J. E. Avron et al., Phys. Rev. Lett. 93, 186001 (2004); D. Tam and A. E. Hosoi, Phys. Rev. Lett. 98, 068105 (2007)].

However this is only part of the problem. The second requirement for a successful swimmer is an actuation mechanism for generating the shape sequence, and the requisite energy. This question still remains largely unresolved, with a few proposed mechanisms holding promise, such as mechano-chemical coupling in elastic membranes [R. Lipowsky, in Statistical Mechanics of Biocomplexity (Springer, Berlin, 1999), vol. 527 of Lecture Notes in Phys., pp. 1-23; P. G. Petrov et al. Europhys Lett. 48, 435 (1999)] or the use of magnetic [K. Ishiyama et al. Sens. Actuators, A 91, 141 (2001)] or electric fields [S. T. Chang et al., Nature Materials 6, 235 (2007); Y. Osada et al., Nature 355, 242 (1992)]. Plagiarising from nature is of little help here: the flagellar rotor, for example is an extremely sophisticated piece of machinery, consisting of over 20 components packed in a tiny volume, which is impossible to reproduce with current technology.

Thus there has been a search for simpler mechanisms. The inventors have previously described "Ferromagnetic dipole-pair tweezers for biomedical applications", F. Y. Ogrin, C. P. Winlove and P. G. Petrov, at the joint $10^{th}$ MMM/Intermag Conference in Baltimore in 2007, 7-11 Jan. and speculated that these might be used for swimming. However the inventors later discovered that the device they described would not work as a swimming device. An interesting theoretical approach is described in Najafi et al. (ibid). A practical swimming device has been described in a number of papers by Ishiyama and colleagues (ibid) and also, for example, T. Honda, K. I. Arai, K. Ishiyama, "Micro swimming mechanisms propelled by external magnetic fields," IEEE Trans. Magnetics, vol 32, issue 5, pp. 5085-5087, September 1996; IEEE Trans. Magnetics, vol. 41, No. 10, pp. 4012-4014, pp. 4021-4023 and pp. 4191-4193 (2005) and JP 2001-179700. Broadly speaking this device comprises a magnet attached to a helical of wire which is propelled through a medium by magnetic torque. The first artificial microswimmer with a flexible flagellum-like tail has also recently been assembled [R. Dreyfus et al., Nature 437, 862 (2005). However, it is still a complicated assembly of magnetic particles bridged by DNA molecules and attached to a red blood cell, which makes the routine production of this type of swimmers untenable. Further background prior art can be found in US 2006/196301 and US 2005/029978.

There is, however, a need for improved microrobotic magnetic devices, in particular for swimming through a medium at low Reynolds number, for example for transporting material or, say, performing surgery.

SUMMARY OF THE INVENTION

According to the present invention there is therefore provided a method of propelling a magnetic device relative to a fluid, preferably, at a Reynolds number of less than one. The magnetic device comprises a pair of magnetic moments linked by an elastic coupling element, one of said moments having a greater resistance to a change in orientation due to an external applied magnetic field than the other. The method comprises applying a changing magnetic field to the device to cause a change in mutual attraction or repulsion between said magnetic moments to thereby change a physical configuration of said device, propelling said device through said fluid. Preferably the field comprises an elliptically rotating field, preferably with an eccentricity of greater than 0.5, 0.6, 0.7, 0.8 or 0.9.

In embodiments the magnetic device may swim through the fluid (which may itself be flowing) or it may be tethered, attached or fastened in any convenient manner, such that the fluid is drawn past the device, thereby pumping the fluid through the conduit from one location to another. Thus a pump may be constructed using the method. Such a pump may have the magnetic device tethered in a conduit for the fluid, such as a pipe or channel or opening between, say, two chambers. It will be appreciated that such a pump may be very small, for example of one or more dimensions less than $10^{-3}$ m, $10^{-4}$ m, $10^{-5}$ m or $10^{-6}$ m, making such a pump useful, for example, in microfluidics applications.

Embodiments of the method use changing attraction between the magnetic moments to drive a cyclic deformation of the device which (in part) propels the device through the fluid. This is in contrast to, say, attempting to drag the device through the fluid by application of an external magnetic field gradient—embodiments of the method can be performed in a substantially uniform magnetic field—and this in turn enables a reduction in the overall applied field. Embodiments of the technique may be employed at macroscopic scales, for example with devices having a dimension of greater than 1 millimeter or even greater than 10 millimeters; however embodiments of the technique are particularly advantageous in that they may be scaled down to devices with a maximum dimension of less than $10^{-3}$ m, $10^{-4}$ meters, $10^{-5}$ m or even $10^{-6}$ m. Furthermore it has been found that fabrication of a working device is very straightforward—the technique appears to be extremely robust to a selection of materials, magnetic field conditions and the like.

In some preferred embodiments the magnetic moments comprise magnetic dipoles, in particular ferromagnetic dipoles although other types of magnetic ordering may also be employed and, potentially, also magnetic materials without a spontaneous magnetic ordering such as a superparamagnetic material (which acquires a magnetic moment in a magnetic field). Theoretically, in say, a dielectric fluid an externally applied electric field and/or electric rather than magnetic moments might be employed.

In some preferred embodiments of the method, the magnetic device comprises two magnetic particles or elements (in this context elements referring to parts of the device rather than to chemical elements), one of these having a different shape and/or composition to the other. Thus in embodiments one of the magnetic particles comprises a hard magnetic material, for example with a coercivity of greater than 1000 Oe, 1500 Oe, 5K Oe or 10K Oe and the other of the magnetic particles comprises a soft magnetic material, for example with a coercivity of less than 1500 Oe or less than 1000 Oe, 500 Oe, 200 Oe, 100 Oe or 50 Oe. Additionally or alternatively, a difference in anisotropy between the magnetic particles may be provided by giving the particles different shapes (shape anisotropy), for example providing one or both particles with a long axis to define a preferred magnetisation direction. As previously mentioned, embodiments of the method appear to be robust with respect to the selection of materials; some example hard magnetic materials include some steels, alnicos, hard ferrites, and various rare earth—based magnets; example soft magnetic materials include some steels, various iron alloys, soft ferrites, nickel, cobalt and Permalloy (RTM).

A related method may be employed to provide mechanical work from the pair of magnetic moments, for example for a miniature pump or motor or to provide a pair of magnetic tweezers. In such a system the elastic coupling element may be provided by a biological object to be studied or manipulated, for example a cell or protein molecule. However preferably the method is employed to propel the magnetic device through the fluid, and hence provide a magnetic "swimmer".

Broadly speaking in such methods of magnetic swimming the magnetic field is rotated to provide a combination of two different motions in the magnetic device, a first arising from a change in magnetic attraction/repulsion between the magnetic moments due to their differential resistance to change and orientation, and a second arising from an overall torque on the magnetic device. The combination of these two motions results in translation of the device through the fluid, that is "swimming". There need not be a spatial gradient in the applied external magnetic field since, in embodiments the device is not being dragged through the fluid, rather it is the motions of the device induced, in part, by attraction/repulsion of the different portions of the device in response to the changing external field, which propels the device through the fluid.

The dynamics of the device (described later) are relatively complicated but it has been found that preferably the device is configured such that different regions of the device have a different resistance to motion in the fluid. More particularly a region "driven" by one of the magnetic moments should have a different resistance to motion in the fluid of a region driven by the other of the magnetic moments. This helps to achieve overall translation or motion through the fluid. Conveniently this can be achieved by providing particles which are the sources of the respective magnetic moments with a different shape and/or size (in at least one dimension) and/or volume. In embodiments the harder magnetic particle, with the greater magnetic anisotropy, may be larger or have the greater viscous resistance. Thus in embodiments time asymmetry can be broken by, inter alia, using particles of different sizes or volumes, or magnetic moments or both.

A wide range of elastic couplings may be employed but in some preferred embodiments the elastic coupling may comprise, or consist of, a biological entity such as a cell, protein, or vessicle (optionally incorporating a drug). More generally the method may be employed to transport a drug or a surgical or other instrument, for example within a human or animal body. Embodiments of the method we describe also have many non-medical applications, for example in swimming through pipework and the like.

The invention also provides a method of directing, in particular steering, a magnetic swimming device, swimming according to an embodiment of the method described above. Some detailed techniques are described later and theoretical simulation and practical experiment has shown that it is not obvious how the swimmer will respond to changes in the external magnetic field. For unpredictable changes one approach is to employ feedback from the swimmers orientation and/or direction of motion either, say, optically (if the device can be seen) or using some other wireless technique, for example detecting a signal from the device. Then one or more parameters of the magnetic field may be changed, using the feedback to achieve motion in the desired direction.

In some preferred embodiments, however, an ellipsoidal rotating magnetic field is employed, for example a substantially two-dimensional elliptical magnetic field (elliptical referring to the magnitude and direction of a vector describing the externally applied magnetic field). In such a case it has been found, for a magnetic swimmer as described above, that: An orientation, and hence potentially a direction, of the swimming device can be changed by changing a direction of a major axis of the ellipse (the change in orientation angle of the swimmer is substantially the same as the change in angle of the major axis). Any variation in the degree of ellipticity of the external applied field changes the direction in which the swimming device swims. For an ellipsoidal rotating magnetic field with a defined plane of rotation, a change in the orientation of this defined plane of rotation will result in a change in direction of the swimming. More particularly in embodiments of the method the swimmer swims in the plane of the elliptical field and thus changing this plane changes the plane in which the swimmer swims. Changing the frequency of the rotating field also changes the direction in which the device swims. Still further, contrary to theoretical predictions, but observed experimentally, probably due to magnetisation properties of the particles providing the magnetic moments, varying the amplitude of the externally applied field has also been found to change the direction of swimming.

In a related aspect of the invention there is therefore provided apparatus for propelling and directing a magnetic swimming device through a fluid with a Reynolds number of less than one, the magnetic swimming device comprising a pair of magnetic moments linked by an elastic coupling element, one of said magnetic moments having a greater resistance to a change in orientation due to an external applied magnetic field than the other, the apparatus comprising: a magnetic field generator to generate a rotating magnetic field to propel said magnetic swimming device through said fluid; and a magnetic field control system to control said rotating magnetic field to thereby direct a motion of said magnetic swimming device through said fluid.

Thus a system for propelling and directing a magnetic swimming device may include apparatus as described above, and a magnetic swimming device as described later. As previously described, in preferred embodiments the rotating magnetic field comprises an ellipsoidal, in particular elliptical rotating magnetic field and the directing comprises altering one or more properties of the ellipsoidal (or elliptical) field. One or more of these properties may be altered by a change in physical configuration of the apparatus, for example where the magnetic field generator comprises one or more pairs of coils such as Helmholtz coils, an orientation of these coils may be adjusted. Additionally or alternatively a controllable signal generator may be employed with a fixed set of 3D coils to control and define the rotating magnetic field in essence in a system with, say, two or three pairs of coils the relative amplitude and phases of currents through the coils are controlled such that the resultant magnetic field vector from the pairs of coils combines to define the desired rotating magnetic field.

In another aspect there is provided a magnetic device, in particular for operation in a fluid at a Reynolds number of less than one, the device comprising: a first magnetic particle to provide a first magnetic dipole; a second magnetic particle to provide a second magnetic dipole; and an elastic coupling mechanically coupled between said first and second magnetic particles; and wherein along an axis joining said first and second magnetic particles said first magnetic particle has a greater magnetic anisotropy than said second magnetic particle.

In embodiments the particles are asymmetric in either size, or magnitude of magnetic moment, or both. In preferred embodiments the device operates at a Reynolds number of less than $10^{-1}$, $10^{-2}$, $10^{-3}$ or $10^{-4}$. It will be understood that, in embodiments, the device may include more than two magnetic particles, depending on the configuration of the device. Broadly speaking the magnetic anisotropy is a measure of the energy required to move a magnetisation along the axis joining the particles away from this axis, broadly a difficulty in changing a component of magnetisation along this axis. As described above, because this is different for the two particles, in a changing, in particular rotating magnetic field the device swims by changing its orientation relative to a fixed coordinate system (for example its orientation relative to the fluid) and by changing a distance between the first second and magnetic particles. Preferably the device is driven by a magnetic field of exchanges in both magnitude and direction, that is an ellipsoidal, more particularly an elliptical magnetic field as described above.

In preferred embodiments one of the particles, for example a particle with greater intrinsic coercivity (a harder magnetic material) is bigger, or is configured to have a greater viscous resistance in the fluid, than the other.

In embodiments the elastic coupling has a greater bending modulus than a Young's modulus of elasticity of the coupling along its axis. In embodiments the elastic coupling is substantially resistant to bending perpendicular to the axis joining the particles. Thus in embodiments the elastic coupling may have the shape of a spheroid, ring or loop—that is the elastic coupling may extend in a direction perpendicular to the axis having, say, a width to length ratio of at least 0.2, 0.3, 0.5, 0.7 or 1. In embodiments the separation between the magnetic particles is greater than a maximum dimension of at least one of the particles; a coupling length may be, for example, more than 2, 5 or 10 times the size of particle. Preferably the coupling provides a resilient bias to oppose compression caused by magnetic attraction between the particles. In some embodiments the elastic coupling may comprise a plastic or rubber ring, loop or other structure.

However in other embodiments the elastic coupling may comprise organic material or a biological entity, for example a cell, protein, macro molecule, vessicle, lipid bilayer or the like. The skilled person will understand that there are many well-known techniques for attaching particles to such material including (but not limited to) for example an antibody-antigen reaction, or a streptavidin-biotin link or, in the case of an artificial membrane such as a lipid bilayer, it has been found that magnetic particles will spontaneously attach to and/or be incorporated within such a membrane. In the case of a vessicle or lipid bilayer material such as a drug may be incorporated within the structure, which can then be destroyed in order to release the material.

In a related aspect the invention provides a magnetic swimming device for swimming in a fluid at a Reynolds number of less than one, the swimming device having at least two degrees of freedom of motion in said fluid, a first degree of freedom comprising a change in dimension of at least a part of said device and a second degree of freedom comprising a rotation of at least a part of said device with respect to said fluid, the device having at least two parts with different magnetic properties such that, when a changing magnetic field is applied, said device executes non-reciprocal motion over said two degrees of freedom of motion to thereby propel said device through said fluid.

The invention further provides a method of propelling a magnetic device through a fluid at a Reynolds number of less than one, the method comprising: applying a magnetic field with a changing direction to the device to cause the device to execute time-asymmetric motion in said fluid with at least two degrees of freedom, said motion including a change in orientation of the device with respect to the fluid and a change in a configuration of the device due to changing internal magnetic forces driven by said applied magnetic field, said time-asymmetric motion causing said device to be propelled through said fluid.

The invention still further provides apparatus for propelling a magnetic device through a fluid at a Reynolds number of less than one, the apparatus comprising a system for applying a magnetic field with a changing direction to the device to cause the device to execute time-asymmetric motion in said fluid with at least two degrees of freedom, said motion including a change in orientation of the device with respect to the fluid and a change in a configuration of the device due to changing internal magnetic forces driven by said applied magnetic field, said time-asymmetric motion causing said device to be propelled through said fluid.

BRIEF DESCRIPTION OF THE DRAWINGS

These and other aspects of the invention will now be further described, by way of example only, with reference to the accompanying figures in which.

DETAILED DESCRIPTION OF PREFERRED EMBODIMENTS

We will describe an artificial low Reynolds number swimmer, based on the magnetic interactions of a pair of ferromagnetic particles, one with hard and the other with soft magnetic properties connected by a preferably linear spring. Using a computational model, we analyse the behaviour of the system and demonstrate that for realistic values of the parameters involved, the swimmer is capable of self-propelling with average speeds up to of the order of tens or even hundreds of micrometers per second.

Being positioned in close proximity the dipoles are subjected to their own magnetic forces. Under the application of rotating external field the magnetisation of the "hard" magnetic particle is not significantly varied, whereas the magnetisation of the "soft" particle follows the orientation of the field and thus changes cyclically from parallel to anti-parallel orientation with respect to the moments in the "hard" particle. The dipolar force between the particles thus then oscillates leading to attraction and repulsion displacements between the particles. Due to the non-reciprocal nature of the oscillatory motion the displacements result in a linear motion of both particles. In typical conditions for two micron sized magnetic particles submerged in water their overall velocity can reach up to several tenths of microns per second. We describe how the velocity depends on parameters of the system and the optimum conditions. The model accounts for realistic dimensional, hydrodynamic, magnetic and dynamic parameters.

The first ferromagnetic swimmer is a magnetically driven device, which generates linear motion by using non-reciprocal displacement of its components. The design is simple, in embodiments having just three main elements. In embodiments the displacement of the components of the swimmer is not imposed, but is the result of physical interactions between them. Thus, swimming is derived from a realistic actuation mechanism, which, together with the swimmer's simple design and the relatively high displacement velocities achieved, makes it useful for practical implementation. The driving magnetic forces need not originate from the gradient of external fields, but instead the swimmer utilises the forces produced by the magnetic particles themselves.

The basis of the approach is to employ a pair of (preferably) ferromagnetic dipoles (subsequently referred as the 'dipole-pair'), one with hard and the other with soft magnetic properties. The particles are sufficiently close as to interact with each other, and in many applications they may be bound to an elastic element such as a vesicle, a polymer or a protein fibre. The elastic element serves a double purpose. Firstly, it acts as a coupling to maintain an average separation between the particles, and secondly it may constitute the 'transported' object in applications aimed at targeted delivery (e.g., a giant vesicle loaded with an active agent).

Figure 1:
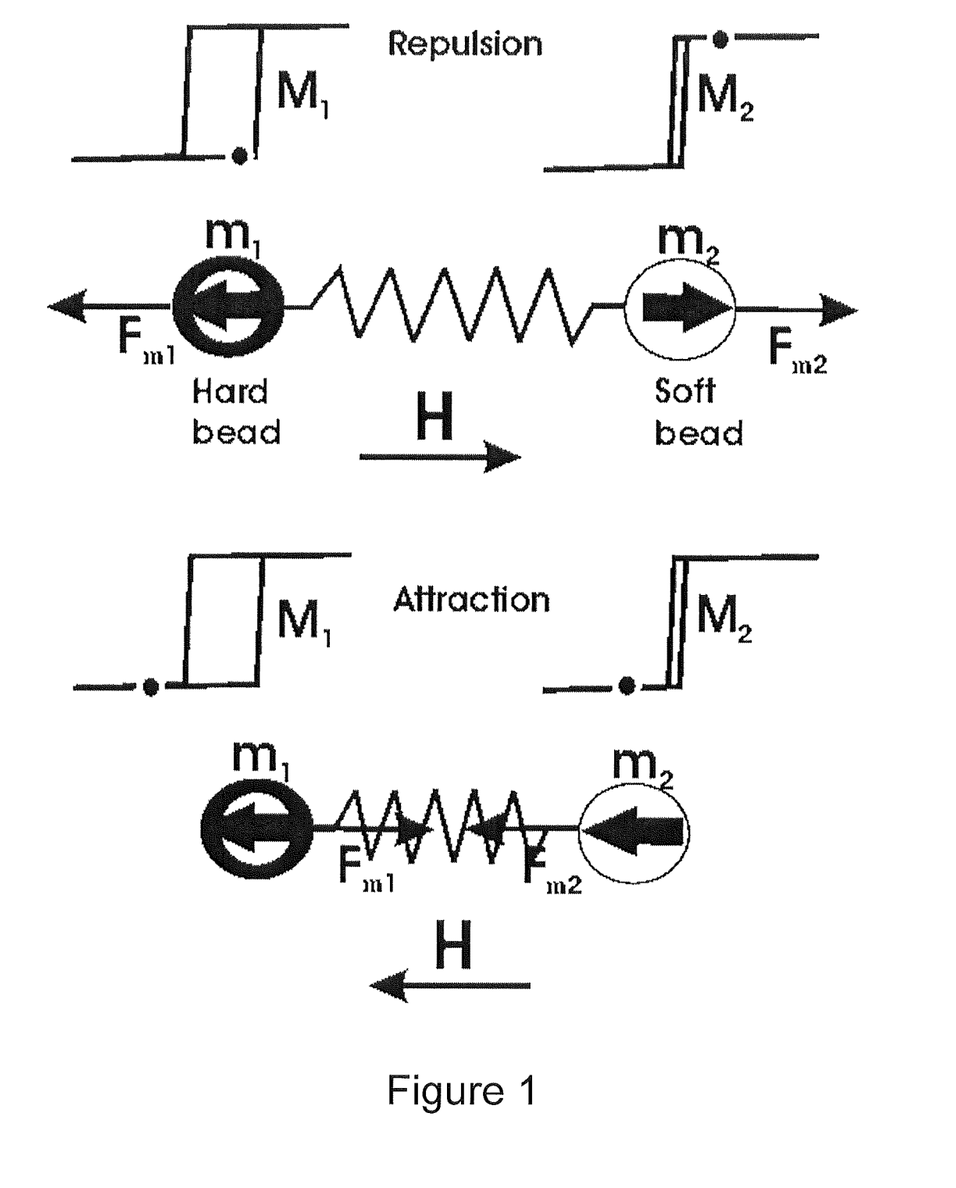
FIG. 1 shows a schematic representation of intra-system forces in a model of a magnetic device according to an embodiment of the invention.

The dipole-pair is subjected to an alternating uniform external magnetic field, allowing a hysteresis-dependent orientation of the average magnetic moments. In embodiments the amplitude of the external field is chosen to be sufficient to change (switch) the orientation of the soft particle, but preferably lower than the switching field of the hard particle. Thus the two particles will respond differently to changing the direction of the external field. In general the soft particle will always direct its moment along the field, whereas the hard particle will keep the moment close to the initial position of equilibrium (i.e. the local energy minimum). FIG. 1 shows a diagrammatic representation of a system comprising hard and soft magnetic particles connected by an elastic element. The magnetic forces experienced by the two particles are shown for two orientations of the external magnetic field, H. As demonstrated in FIG. 1, in a simplified case when the external field axis coincides with the line connecting the two dipoles, and is parallel to the anisotropy directions of the particles, the alternating magnetic field will produce alternately changing configurations with either parallel or anti-parallel orientation of the magnetic moments. Consequently, due to the local gradient of the magnetic fields produced by the moments, the particles will be subjected to an alternating force of attraction and repulsion, leading to translational displacements along the line connecting the particles.

The motion of the particles is in this case reciprocal, since the system possesses only a single degree of freedom, so the dipole-pair moves or oscillates around a fixed centre. This type of motion can be utilised in experiments in which elastic deformation of a biological object is studied. For instance this system is useful for holding, manipulating and/or studying elastic properties of protein molecules, cell membranes, or cells such as red blood cells. However, in order to achieve translation of the centre of mass of the dipole-pair the system has to undergo non-reciprocal cyclic displacements in its configurational space. One preferred approach is to introduce an elliptically rotating uniform magnetic field in the xy-plane, $H_x=H_x^0 \cos(\omega t)$ and $H_y=H_y^0 \sin(\omega t)$, where $\omega$ and t represent the angular frequency and time respectively, and $H_x^0$ and $H_y^0$ are the horizontal and vertical amplitudes of the field ($H_y^0 < H_x^0$). In this case the external field vector is rotated in the plane of the two dipoles. The magnetisation of the soft particle follows the field direction, whereas the magnetisation of the hard particle only slightly 'rocks' around an established average orientation. The resultant effect is that the particles are again repelled and attracted, however this time the instant displacements of the particles are much more complex leading to a non linear trajectory of motion.

To investigate such a system the inventors have developed a computational model, which calculates the trajectories of the two particles under conditions of environment and geometry that provide a realistic representation of possible microscopic swimmers. The model is based on the assumption that both magnetic beads are 'point dipoles' and thus will generate a dipole magnetic field, the gradient of which will result in a force of attraction or repulsion between the beads:

$$F_{Mj} = \nabla(m_j \cdot B_k),$$
$$B_k = \frac{\mu_o}{4\pi}\left(\frac{3(m_k \cdot r_k)r_k}{r_k^5} - \frac{m_k}{r_k^3}\right),$$

where $B_k$ is the flux density generated by the bead k, $m_k=M_k/V_k$, and $M_k$, $V^k$ and $r_k$ are the magnetization, volume and position vector of the beads j and k respectively (indices denote the particle number, j=1 or j=2 and k=3−j, see FIG. 1). To determine the orientation of the dipole moments in the external applied field H the model uses a magnetostatic approach [see for example G. Bertotti, Hysteresis in Magnetism (Academic Press, Inc., San Diego, 1998)], in which the interaction energy is minimized to find the local minima with stable positions of both moments.

For simplicity, the magnetostatic energy density for each particle is represented by two terms, $E=-M\cdot H+K \sin^2 \alpha$. The first term is the Zeeman energy representing the interaction of the magnetic moments with the applied field H, and the second, the uniaxial magnetic anisotropy term, describes the combined effects of shape and/or crystalline anisotropy. In the latter, $\alpha$ is the angle between the magnetic moment of the particle and the orientation of its easy axis with respect to vector M, and K is the effective anisotropy field constant. In the model, for the hard particle K is chosen so that the effective anisotropy field is higher than the value of the applied field (2K/M>H), whereas the soft particle has a zero value of K. It is assumed that the time-scale of magnetic switching/relaxation (<1 ns) is significantly shorter than the timescale associated with the time-period of the applied field oscillation ($\approx$1-10 ms).

It should be noted that having different anisotropy constants for the beads is important not only for obtaining different switching characteristics, but also for generating asymmetric torques on the particles. Under the action of magnetic torque, $T=\mu_0 m \times H$, the particle with higher anisotropy can rotate to align its easy axis with the direction of the applied field. If the particles are connected, preferably rigidly, with each-other, the torque applied to the hard particle will tent to rotate the whole dipole-pair, which provides another degree of freedom in the configurational space of the system. The soft particle does not contribute to the torque. Its anisotropy is preferably negligible, so the rotation of its magnetic moment does not substantially affect the orientation of the pair.

As well as the magnetic interaction both beads are also subjected to elastic forces and hydrodynamic friction. The elastic force, $F_E$, results from the extension/compression of the elastic element connecting the two particles, $F_E=k_s[(r2-r1)-r0]$. Here $k_s$ is an effective spring constant and $r_0$ is the vector representing a relaxed spring. The bending modulus of the spring is assumed, in the model, to be infinitely large. The viscous resistance, acting on each particle, is calculated using the Stokes approximation, in which the drag force FD is proportional to the particle velocity v, radius R, and the viscosity of the fluid $\eta$, $F_D=-6\pi\eta Rv$.

Figure 2:
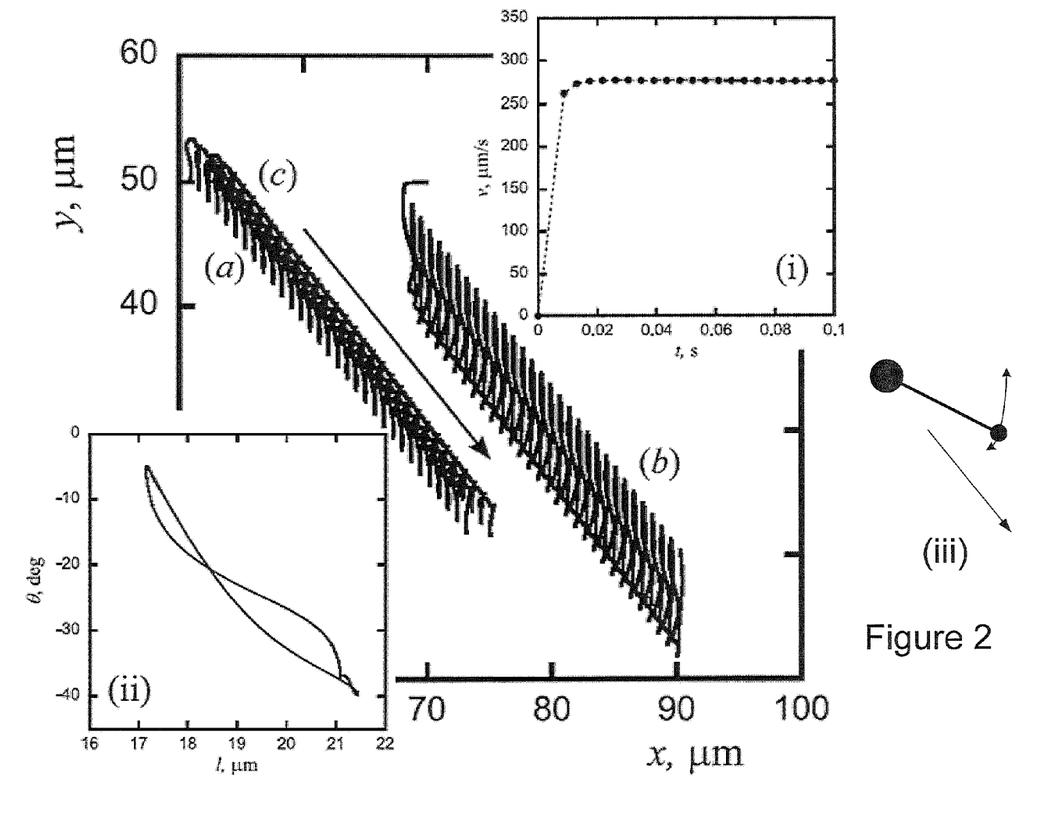
FIG. 2 shows trajectories of features of a magnetic swimming device according to an embodiment of the invention in an elliptically rotating externally applied magnetic field, together with a calculated mean velocity of the device (inset (i)), and a trajectory of the magnetic swimming device in configuration space (inset (ii))

The motion of the system has been calculated for realistic parameters of the liquid (water, $\eta=10^{-3}$ Pa s) and the dipole-pair system (magnetic particles of 3.2 and 1.6 µm diameter connected by a 20 µm long elastic element with $k_s=3\times10^3$ N m$^{-1}$). FIG. 2 shows the trajectories of the particles together with that of their centre of mass. More particularly (FIG. 2 shows trajectories of the hard bead (a, lower), soft bead (b, upper) and their centre of mass (c, mid) after application of an elliptically rotating external field (curve (c) broadly follows curve (a), albeit with reduced excursions and displaced slightly upwards from curve (a) in the Figure). As well as rapid oscillatory motion the dipole-pair follows a directional linear displacement ('swimming') along the arrow towards the lower-right corner. Inset (i) shows the mean velocity of the centre of mass as a function of time. Inset (ii) shows the trajectory of the swimmer in its configurational space where $\theta$ is the angle between the elastic element and the horizontal axis and 1 is its instantaneous length. The parameters of the simulation are $H_y^0=1$ kOe, $H_x^0=5$ kOe, $f=230$ Hz, $2K_1/M_1=10$ kGs, $2K_2/M_2=0$ kGs, $M_1=M_2=1.4\times10^6$ A m$^{-1}$, $2R_1=3.2$ µm, $2R_2=1.6$ µm, $r_0$ (relaxed spring length)=20 µm, $k_s=3.0\times10^{-3}$ N m$^{-1}$, $\eta=10^{-3}$ Pa s, Re$\approx 10^{-3}$.

Thus it can be seen that as well as the motion of the individual particles there is a linear displacement, or "swimming", of their centre of mass, with an average speed shown in inset (i). Inset (ii) shows the trajectory in the configurational space of the systems with coordinates 1 (the distance between the centres of the two magnetic particles) and $\theta$ (the angle of the bond between them with respect to the horizontal axis) forming a closed loop. After a full cycle the original configuration of the system is recovered, but the system shape sequence executed is non-reciprocal, thus the conditions for swimming are fulfilled allowing a net translation of the centre of mass.

Figure 3A:
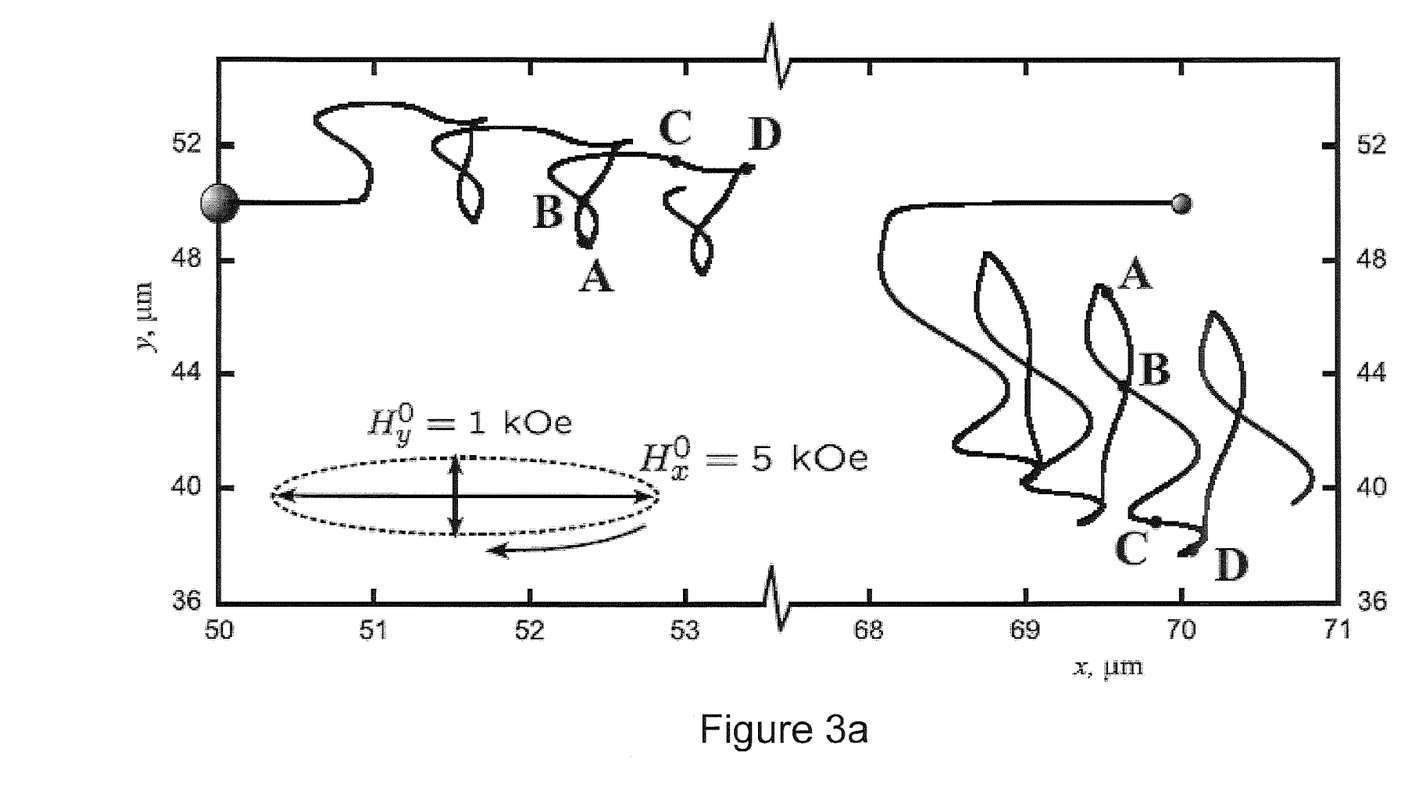
FIGS. 3a and 3b show, respectively, particle trajectories in a magnetic device swimming according to a method embodying an aspect of the invention, and, schematically, snapshots of the particles of the device as successive points in a swimming cycle.
Figure 3B:
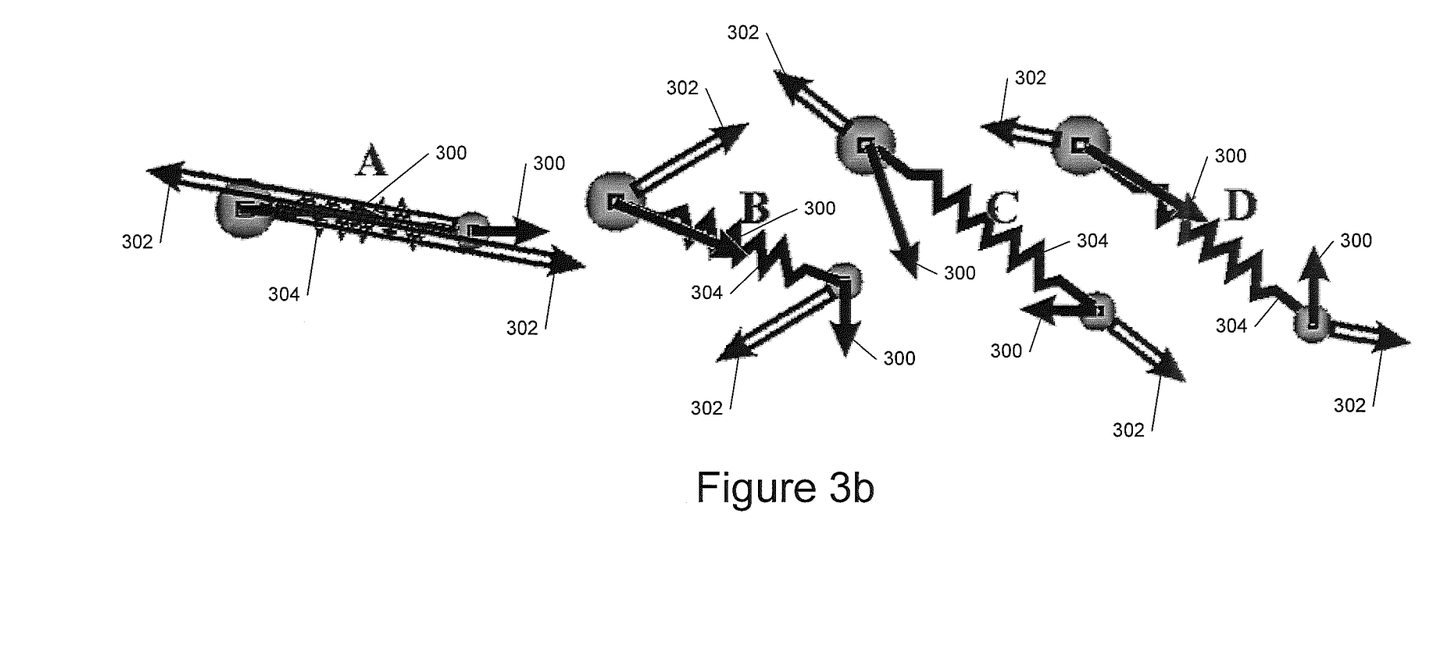

FIG. 3a shows particle trajectories (solid lines) at different phase of the field cycle. The schematic diagram of FIG. 3b shows the orientations of the magnetization for each particle (solid arrows 300), the magnetic gradient forces (double line arrows 302), and the orientation of the dipole-pair at the same points of the cycle (the magnetization of the smaller, soft particle follows the external magnetic field). The anisotropy easy axis of the hard particle coincides with the line (spring 304) connecting the particles. The size of the particles and their separation are exaggerated for clarity.

FIG. 3 demonstrates the different phases over one cycle together with the corresponding orientation of the magnetic moments and the magnetic dipolar gradient forces. In general, the overall displacement of the system results from the asymmetry related to the different 6 degree of rotation provided by the torque at different stages of the external field cycle and the varying distance between the particles.

The trajectory of motion and thus the characteristics of swimming of the dipole-pair depend on the parameters of both the particles and the external environment. In some preferred embodiments the particles have different size, and the time variation of the external field does not lead to full rotation of the hard bead. The latter requirement can be achieved by choosing an appropriate value for $H_y^0$. This results in linear motion. It is interesting to note the significance of the torque in this system, which provides a mechanism for overall displacement of the dipole-pair. Without the torque, even if the external field is rotated, there is no displacement of the centre of mass. In this case the particles oscillate in phase with the field, but the centre of mass is either stationary, if the particles are of the same size, or otherwise oscillating, but not producing directional motion. Generating a large torque, on the other hand, leads to a circular rotation (instead of 'rocking') of the hard particle, thus inhibiting linear motion.

Figure 4:
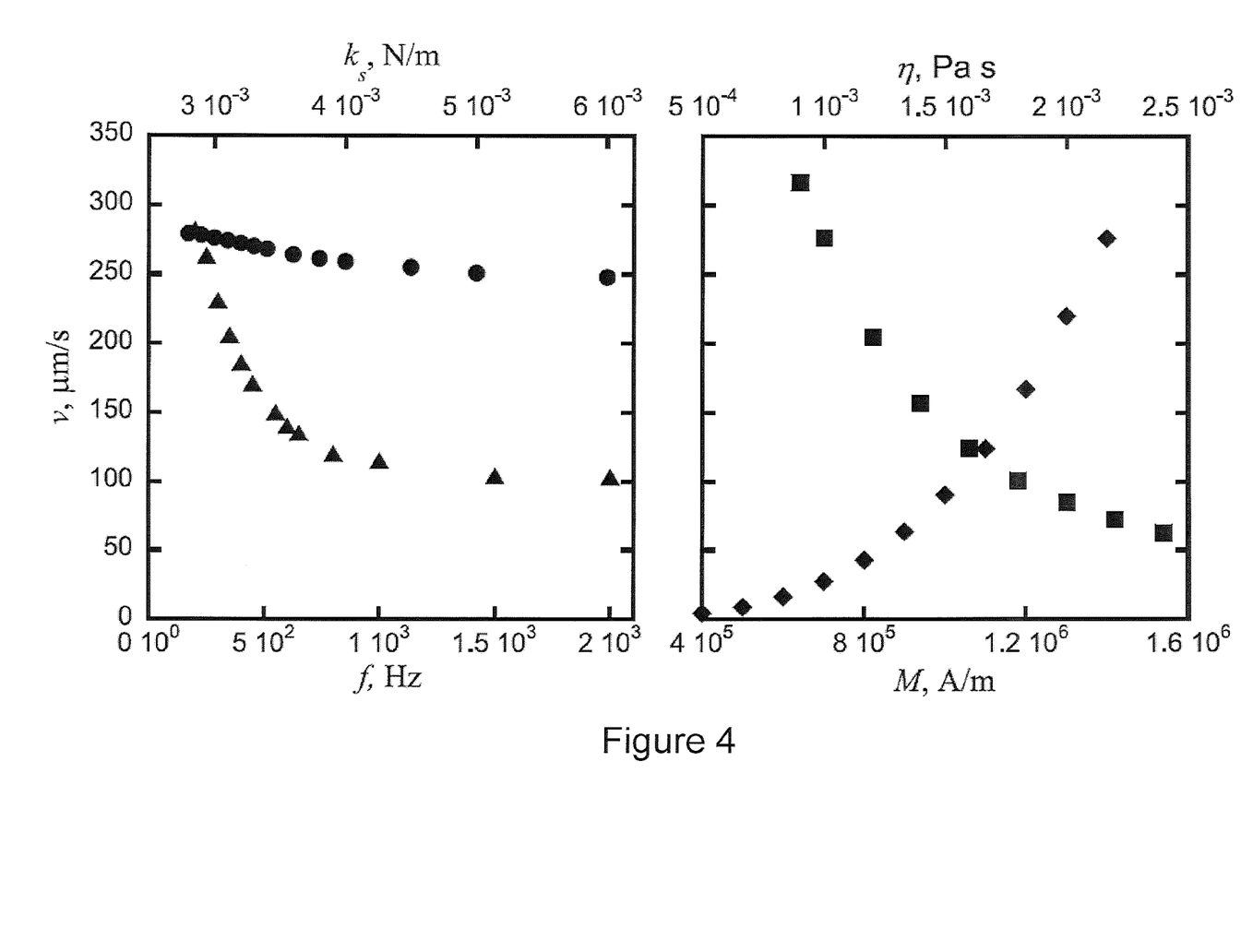
FIG. 4 shows graphs of translational velocity of a magnetic swimming device according to an embodiment of the invention as a function of parameters of the magnetic swimming system.

FIG. 4 shows the calculated velocity of translational displacement of the swimmer as function of some of the parameters: spring constant $k_s$ (circles), frequency f (triangles), magnetization $M_1=M_2$ (diamonds) and viscosity η (squares). The values of the other parameters are as described with reference to FIG. 2.

Thus FIG. 4 demonstrates the dependence of the linear translational velocity of the dipole-pair on magnetization, M, frequency, f, spring coefficient, $k_s$ and viscosity of the liquid, η, for the system described in FIG. 2. The velocities cover a broad range, providing flexibility in controlling the swimming. Compared with the average velocities produced by micron-sized organisms such as E. coli ($\approx 30$ μm s$^{-1}$, the speed generated by the magnetic dipole-pair can be up to an order of magnitude higher. The simple model described above involves a number of idealizations. The elastic element is assumed to stretch and contract along the principle axis. Bending is not included, although for a real device this will add a certain degree of complexity. We have also disregarded the geometry and the size of the element, which in real system will lead to an increased hydrodynamic interaction. These simplifications, however, do not affect the principles of swimming, they affect only the characteristics. By balancing the parameters of the system it is possible to optimise the swimming characteristics. For instance, the reduction of the angular rotation of the spring (because of the non-zero dimensions) can be counter-acted by increasing the magnetic torque (e.g. by increasing $H_y^0$ or increasing the magnetization or anisotropy constant of the material used). A further simplification has been made in setting K=0 for the soft particle. In real materials K will be non-zero, so the soft particle will also rotate in the field. This in turn may counteract the torque produced by the hard particle. However, because the anisotropy of the hard particle can always be chosen larger than that of the soft particle, the torque produced by the hard particle can always be made larger. In addition, the torque can be increased by making the volume of the hard particle larger.

In the current model we disregard the hydrodynamic coupling between the particles. With the large separation between them ($\approx 20$ times the particle radius) chosen for the simulation, the forces produced due to the hydrodynamic interaction are negligible. However bringing the particles closer (separation of about $\approx 5$ times the radius or less) will result in an increased hydrodynamic interaction, which may affect the trajectories of the particles and the velocity of the swimmer. The overall linear motion will be still maintained, but modified in detail. Although the model described here represents a microscopic swimmer (for example magnetic particle dimensions less than $\sim 1$ μm or 100 μm) and all parameters of the materials and the environment have realistic values, the range of existing magnetic materials and easily realised magnetic fields should enable the development of a macroscopic device as well (for example magnetic particle dimension 10 μm or 100 μm to 1 mm or 10 mm or greater). This provides further practical applications and is also of value in experimental tests of the model.

We next describe control of the direction (and orientation) of a magnetic swimming device according to an embodiment of the invention, in particular for steering the swimming device.

In general, the orientation of swimming depends on a number of factors, including anisotropy and magnetisation of the hard and the soft particle, their geometrical dimensions, average separation (length of the coupling element), elasticity of the coupling element, viscosity of the liquid and the parameters of the external magnetic field (orientation of the main axis ($H_x$), ellipticity ($H_{x0}/H_{y0}$), amplitude and frequency). For a chosen dipole-pair and the environment (viscosity), immediate control of the swimming orientation can be achieved by varying the external field parameters. As has been observed in simulations the swimmer will respond to the following variations:

- A change in the direction of the main axis ($H_x$) (for instance by rotating the Helmholtz coils) will result in the change of the orientation of the swimming (by the same angle). The velocity will remain the same.
- A variation of the frequency (ω) of the external magnetic field will result in a change of the swimmers velocity and the angle to the main axis (alpha).
- A variation of the ellipticity of the external field (i.e. changing $H_y$ component at a fixed value of $H_x$) will also change the velocity and the angle of the swim.
- A variation of the amplitude of the external field may also lead to the change in direction. (This is not predicted by the theoretical model, because the particles are always assumed to be in a saturated condition. In real conditions this may not be true so can also lead to variation in the swimming orientation and its velocity, as has been in fact observed on the macroscopic prototype).
- Introducing a 3D variation of the magnetic external field (i.e. introducing $H_z$ component) will also change the orientation of swimming. In this case there are two possible scenarios: One, the net component of the field is still oscillating in one plane (which is now not in the x-y plane), so the change of the swimming direction should follow the plane of the field directions. Second: the net component follows a more complex 3D pattern (e.g. a 'corkscrew'), in which case the swimming direction will depend on the exact form of this pattern. (This latter case has many possibilities and it is difficult to reliably predict an outcome).

The uniform external magnetic can be obtained by a set of two pairs of Helmholtz coils (one pair per each orientation in space). In order to rotate the plane of the field, or use a 3D pattern, a third set of pairs can be used. The field is excited in such a way that the net component (resultant) follows an 'elliptical' rotation in a defined plane of rotation. For instance for the rotation in x-y plane the field components should follow the following set of equations:

$H_x(t)=H_{x0} \cos(\omega t)$ and $H_y(t)=H_{y0} \sin(\omega t)$ where w is the cyclic frequency of oscillations of current in the coils (the coils should be synchronised) and $H_{x0}$ and $H_{y0}$ are the amplitudes of the maximum field intensity produced by the corresponding Helmholtz pairs. In the model we used ellipticity parameter $H_{x0}/H_{y0}=5$, in the test experiment, with only one Helmholtz pair available, ellipticity was much high ($H_{y0}\sim0$). Reducing ellipticity should increase the speed of the swimmer. However, too low values (<5) may cause rotation rather than swimming.

Figure 5:
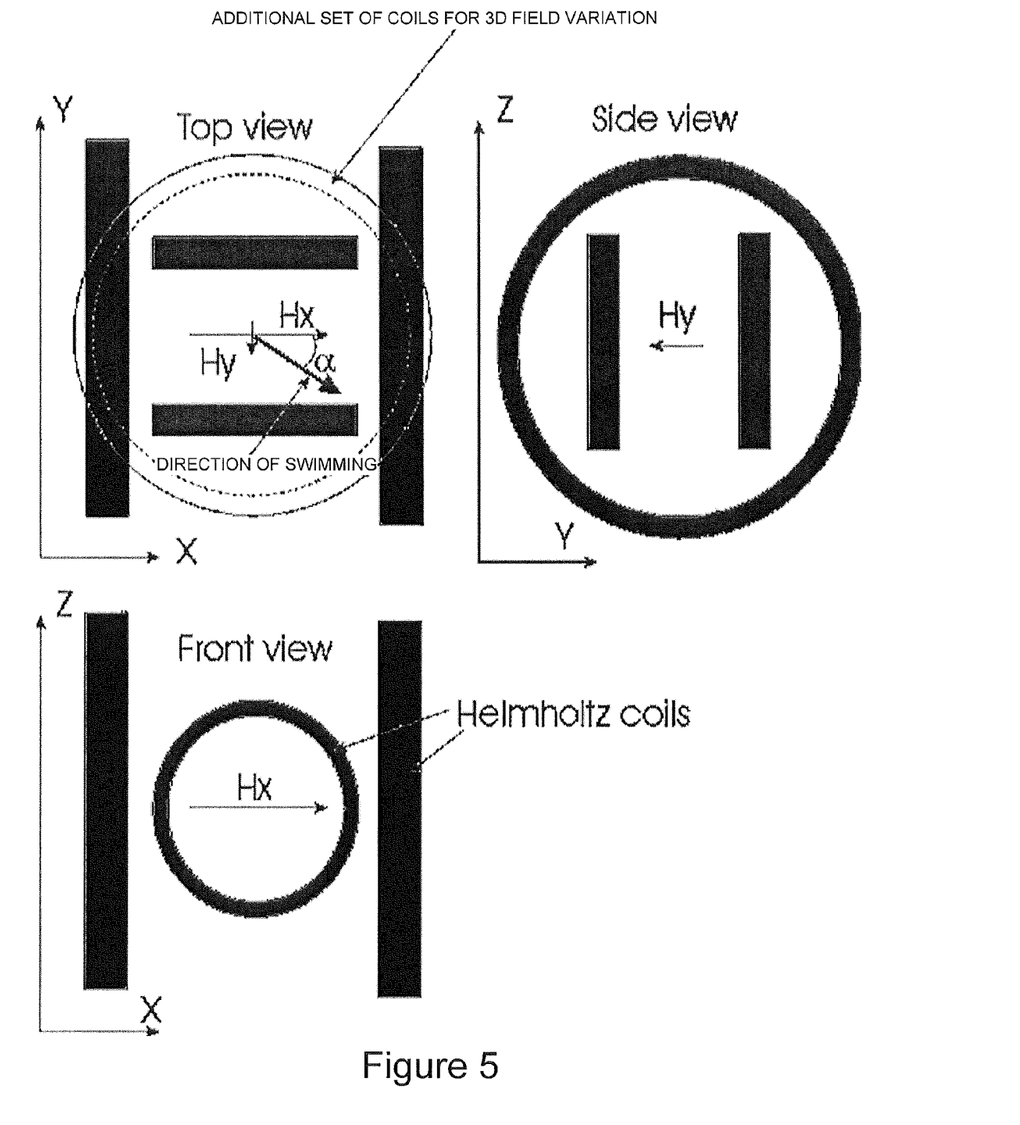
FIG. 5 shows, schematically, apparatus for controlling direction and orientation of a magnetic swimming device according to an embodiment of the invention.

FIG. 5 shows an example arrangement of the external magnetic field and the orientation of swimming Two, optionally three sets of Helmholtz coils are employed to provide a low frequency (of order hundreds of Hertz) 3D vector field magnetic drive system. The three sets of coils may be driven by three signal generators (or a single signal generator with three outputs), each providing a current through a set of Helmholtz coils; in embodiments the magnitude and phase of each current is adjustable and may be set, for example, by a computer system coupled to the signal generator(s).

Figure 6:
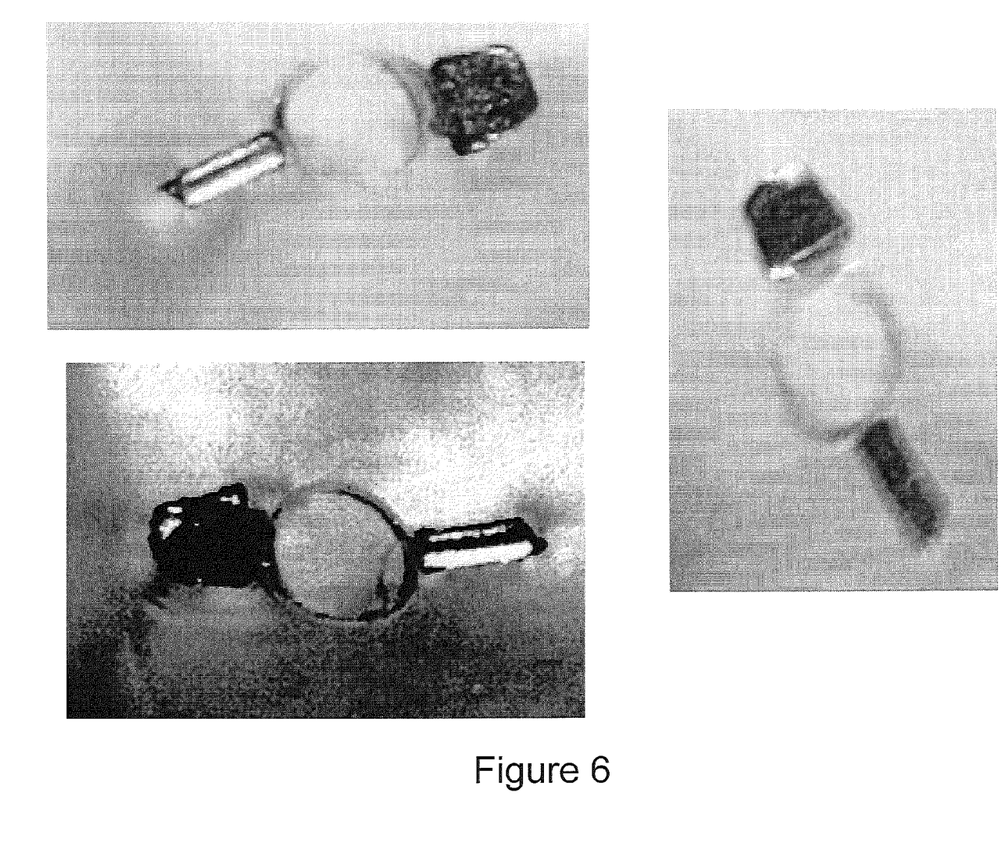
FIG. 6 shows example photographs of an actually constructed prototype device swimming in a variety of different directions (the photographs of FIG. 5 all have the same orientation with respect to an external coordinate system).

Referring now to FIG. 6, this shows photographs of a simple prototype device in which a hard, neodynium magnet (a square shaped magnet) and a soft magnet comprising a short steel pin were linked by a ~1 mm elastic ring (the overall device size was ~3 mm). The illustrated device was swimming in glycerine, in a field of order 100 Gauss (20 cm diameter Helmholtz coils with a 1 cm were employed with a current of order 1 amp to generate, for example, a field of approximately 60 Gauss). In a simple magnetic drive system it has been found that only a single pair of Helmholtz coils need be employed since the generated magnetic field has a degree of ellipticity because such a practical system is imperfect—thus in a simple arrangement a single set of coils may be drive by a sinusoidal AC current with a frequency of, for example, 1-200 Hertz.

Embodiments of the systems and devices we have described have many applications, in particular in the life sciences including, but not limited to, targeted drug delivery, bio-separation, microreactors, cell manipulation, and in general other applications where translational motions and/or local strains on cellular or molecular length scales are useful. In particular, embodiments of the magnetic swimming device may be guided inside or a human or animal body by means of an external magnetic field, for example to perform a surgical procedure or, more straightforwardly, for sensing and/or diagnostic purposes (in the latter cases by means of a signal sent wirelessly from the device, for example by a transmitter). In embodiments, for example with apparatus as illustrated in FIG. 5, the external force may be substantially uniform so that substantially no translational force is generated directly by the external field, instead the device swimming by means of an internal configurational change caused by changes in the attraction/repulsion between the magnetic particles caused by the external applied field. This facilitates the use of lower magnetic fields and might otherwise be needed.

No doubt many other effective alternatives will occur to the skilled person. For example although embodiments of the techniques we describe are particularly useful in addressing the difficult problem of swimming at low Reynolds number they may also be used in situations where Reynolds number is not low. It will be understood that the invention is not limited to the described embodiments and encompasses modifications apparent to those skilled in the art lying within the spirit and scope of the claims appended hereto.

The invention claimed is:

1. A magnetic swimming device for swimming in a fluid, the device comprising:
    a first magnetic particle to provide a first magnetic dipole;
    a second magnetic particle to provide a second magnetic dipole; and
    an elastic coupling mechanically coupled between said first and second magnetic particles;
    wherein along an axis joining said first and second magnetic particles said first magnetic particle has a greater magnetic anisotropy than said second magnetic particle; and
    wherein said first magnetic particle is configured to provide one or both of a greater magnetic moment and a greater viscous resistance to said fluid than said second magnetic particle;
    whereby in a rotating magnetic field said device swims at least in part by changing its orientation and by changing a distance between said first and second magnetic particles.

2. A magnetic swimming device as claimed in claim 1 wherein said first magnetic particle has a greater size in at least one dimension than a size of said second magnetic particle in a corresponding said dimension.

3. A magnetic swimming device as claimed in claim 1 wherein said first and second magnetic particles comprise different respective first and second magnetic materials, and wherein said first magnetic material has a greater intrinsic coercivity than said second magnetic material.

4. A magnetic swimming device as claimed in claim 1 wherein said elastic coupling has a greater bending modulus than Young's modulus of elasticity of said elastic coupling along said axis.

5. A magnetic swimming device as claimed in claim 1 wherein a separation between said first and second magnetic particles is greater than a maximum dimension of at least one of said magnetic particles.

6. A magnetic swimming device as claimed in claim 1 wherein said elastic coupling extends in a direction perpendicular to said axis.

7. A magnetic swimming device as claimed in claim 6 wherein said elastic coupling has the shape of a spheroid or loop.

8. A magnetic swimming device as claimed in claim 1 wherein said elastic coupling comprises an organic material or a biological entity.

9. A magnetic swimming device as claimed in claim 1 carrying a transported object, and wherein said elastic coupling at least in part comprises said transported object.

10. A magnetic swimming device as claimed in claim 1 configured as a pump for pumping a fluid, the pump comprising a fluid conduit and a magnetic swimming device as claimed in claim 1 attached in said conduit such that as said device swims said fluid is transported through said conduit.

* * * * *